(12) United States Patent
Vrckovnik et al.

(10) Patent No.: US 6,407,274 B1
(45) Date of Patent: Jun. 18, 2002

(54) SILICONE AMINE OXIDES

(75) Inventors: Richard O. Vrckovnik; Mark Riddle, both of Toronto (CA)

(73) Assignee: Siltech Corporation, Toronto (CA)

( * ) Notice: Subject to any disclaimer, the term of this patent is extended or adjusted under 35 U.S.C. 154(b) by 0 days.

(21) Appl. No.: 10/025,814

(22) Filed: Dec. 26, 2001

(51) Int. Cl.$^7$ .................................................. C07R 7/10

(52) U.S. Cl. ..................................................... 556/422

(58) Field of Search .......................................... 556/422

(56) References Cited

U.S. PATENT DOCUMENTS

| | | | | |
|---|---|---|---|---|
| 3,197,508 A | * | 7/1965 | Hoffman et al. | ............ 556/422 |
| 4,139,403 A | * | 2/1979 | Baum et al. | ................. 556/422 |
| 4,342,742 A | | 8/1982 | Sebag | |
| 4,663,373 A | * | 5/1987 | Ravichandran et al. | . 556/422 X |

* cited by examiner

Primary Examiner—Paul F. Shaver

(57) ABSTRACT

The present invention relates to silicone based amine oxides. The silicone amine oxides are non-irritating, high foaming products that are substantive to substrates like fiber, metal hair and skin. They also possess good detergency. They are made by reaction of a suitable silicone compound containing an epoxide functionality, followed by reaction with hydrogen peroxide to make the amine oxide.

18 Claims, No Drawings

SILICONE AMINE OXIDES

FILED OF THE INVENTION

The field of the invention is silicone based amine oxides. The silicone amine oxides are non-irritating, high foaming products that are substantive-to substrates like fiber, metal hair and skin. They also possess good detergency.

BACKGROUND OF THE INVENTION

The reaction of tertiary amines, for example of the fatty alkyl-dimethylarine or di-fatty alkyl-methylamine type, with an aqueous hydrogen peroxide solution gives the corresponding tertiary amine oxides. Such amine oxides have good foaming properties and irritate the skin little and can be useful as constituents of cleaning compositions and body care compositions. Tertiary amine oxides are widely used commercially as organic surfactants. Such surfactants have properties that make them very useful in shampoos, hair conditioners, dish and laundry detergents and the like. In these applications, the tertiary amine oxides are employed as aqueous solutions.

U.S. Pat. No. 4,342,742 (Sebag, Vanlerberghe) discloses a silicone amine oxide made through the reaction of a silicone ester from undecylenic alcohol and acetic acid reacted then with a secondary amine. This patent will deal with the silicone amine oxides derived from silicone dialkylaminohydroxy compounds. This is a reaction product of a silicone epoxide with a secondary amine to produce a silicone tertiary amine. This is then reacted with a peroxide to form the amine oxide. The amine oxide provides solubility to the molecule and gives it surfactant properties.

SUMMARY OF THE INVENTION

The present invention relates to a series of silicone based amine oxides. The compounds of the present invention have (a) a silicone portion of the molecule, (b) a fatty portion of the molecule and (c) a polyoxyakylene portion of the molecule. The variation of the ratios of these components alters the performance of the products in terms of foam, substantivity and solubility in oil, water and silicone fluid.

OBJECTIVE OF THE INVENTION

The objective of the present invention is to provide a series of silicone based amine oxides that vary in composition. By proper selection of the raw materials of the resent invention, the process of the present invention can be used to provide a series of silicone amine oxides that have different ratios of (a) silicone portion of the molecule, (b) fatty portion of the molecule and (c) polyoxyakylene portion of the molecule, thereby offering differing functional properties.

DETAILED DESCRIPTION OF THE INVENTION

The silicone amine oxide compounds of the present invention conform to the following structure:

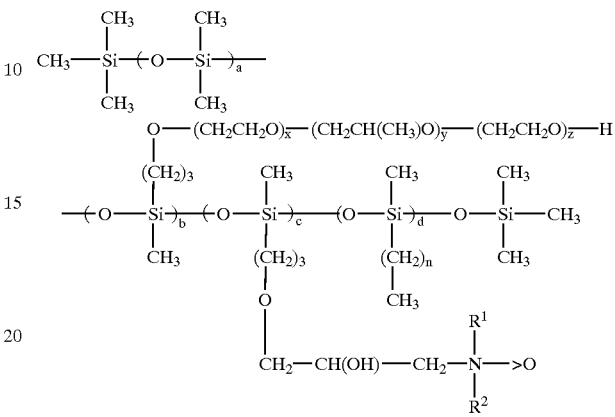

wherein:

$R^1$ and $R^2$ are $CH_3-(CH_2)_e$;

a is an independent integer, each ranging from 0 to 2,000;

b and d are independent integers, each ranging from 0 to 20;

c is an integer ranging from 1 to 20;

x, y and z are independently integers, each ranging from 0 to 20;

n is an integer ranging from 1 to 29.

e is an integer ranging from 0 to 21

Compounds of the present invention are made in two sequential reactions. The first is reacting an epoxy containing compounds conforming to the following structure:

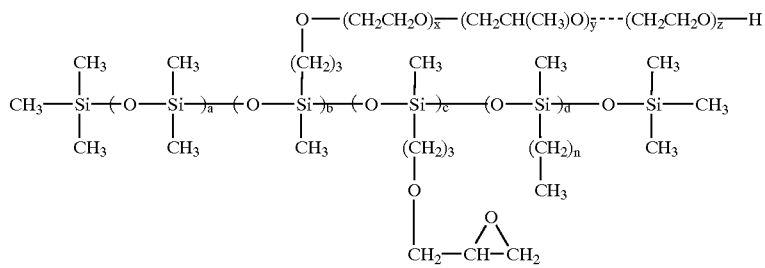

wherein:

a is an independent integer ranging from 0 to 2,000;

b and d are independent integers, each ranging from 0 to 20, c is an integer ranging from 1 to 20;

x, y and z are independent integers, each ranging from 0 to 20.

n is an integer ranging from 1 to 29 with secondary amines conforming to the following structure:

$$R^1\text{—}N\text{—}R^2$$

wherein:
$R^1$ and $R^2$ are $CH_3\text{—}(CH_2)_e$;
e is an integer ranging from 0 to 21.

The reaction of the secondary amine and the epoxy silicone give an intermediate tertiary amine conforming to the following structure;

$$CH_3\text{—}Si(CH_3)_2\text{—}(O\text{—}Si(CH_3)_2)_a\text{—}(O\text{—}Si(CH_3)(R')_b\text{—}(O\text{—}Si(CH_3)(R'')_c\text{—}(O\text{—}Si(CH_3)((CH_2)_n CH_3))_d\text{—}O\text{—}Si(CH_3)_2\text{—}CH_3$$

where $R' = (CH_2)_3\text{—}O\text{—}(CH_2CH_2O)_{\overline{x}}(CH_2CH(CH_3)O)_{\overline{y}}\cdots(CH_2CH_2O)_{\overline{z}}\text{—}H$
and $R'' = (CH_2)_3\text{—}O\text{—}CH_2\text{—}CH(OH)\text{—}CH_2\text{—}N(R^1)(R^2)$ wherein:
$R^1$ and $R^2$ are $CH_3\text{—}(CH_2)_e$;
a is an independent integer ranging from 0 to 2,000;
b and d are independent integers, each ranging from 0 to 20;
c is an integer ranging from 1 to 20;
x, y and z are independent integers, each ranging from 0 to 20;
n is an integer ranging from 1 to 29
e is an integer ranging from 0 to 21.

In the subsequent step the amine is oxidized with hydrogen peroxide to the compound of the present invention.

wherein:
$R^1$ and $R^2$ are $CH_3\text{—}(CH_2)_e$;
a is an independent integer ranging from 0 to 2,000;
b and d are independent integers, each ranging from 0 to 20;
c is an integer ranging from 1 to 20;
x, y and z are independently integers, each ranging from 0 to 20;
n is an integer ranging from 1 to 29
e is an integer ranging from 0 to 21.

$$[\text{tertiary amine silicone structure}] \xrightarrow{+H_2O_2} [\text{amine oxide silicone structure with } CH_2\text{—}N^+(R^1)(R^2)\text{—}O^-]$$

wherein:
R$^1$ and R$^2$ are CH$_3$—(CH$_2$)$_e$;
a is an independent integer ranging from 0 to 2,000;
b and d are independent integers, each ranging from 0 to 20,
c is an integer ranging from 1 to 20;
x, y and z are independently integers, each ranging from 0 to 20;
n is an integer ranging from 1 to 29
e is an integer ranging from 0 to 21.

Preferred Embodiments

In a preferred embodiment b is 0.
In a preferred embodiment b is 1 to 20.
In a preferred embodiment d is 0.
In a preferred embodiment d is 1 to 20.
In a preferred embodiment both b and d are 0.
In another preferred embodiment e is 11.
In another preferred embodiment e is 1.
In another preferred embodiment e is 0.
In another preferred embodiment e is 17.
In another preferred embodiment a is 8, b is 0, c is 4 and d is 0.
In another preferred embodiment a is 4, b is 0, c is 2 and d is 0.
In another preferred embodiment a is 20, b is 0, c is 10 and d is 0

EXAMPLES

The compounds of the present invention are made (1) the reaction of a silicone epoxide with a secondary amine, followed by (2) oxidation of the resulting tertiary amine with hydrogen peroxide to make the amine oxide.

Silicone Epoxide Compounds

The silicone epoxide compounds of the present invention are available from a variety of sources, most important of which is Siltech Corporation of Toronto Ontario Canada. They conform to the following structure;

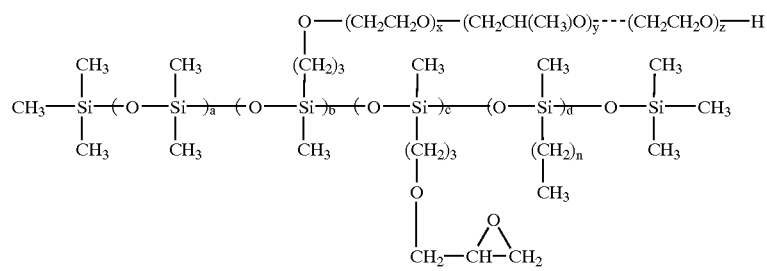

Examples 1–8

| Example | a | b | c | d | n | x | y | z |
|---|---|---|---|---|---|---|---|---|
| 1 | 150 | 0 | 20 | 0 | 0 | 0 | 0 | 0 |
| 2 | 40 | 0 | 10 | 0 | 0 | 0 | 0 | 0 |
| 3 | 8 | 0 | 4 | 0 | 0 | 0 | 0 | 0 |
| 4 | 0 | 0 | 1 | 0 | 0 | 0 | 0 | 0 |
| 5 | 7 | 0 | 5 | 0 | 0 | 0 | 0 | 0 |

-continued

| Example | a | b | c | d | n | x | y | z |
|---|---|---|---|---|---|---|---|---|
| 6 | 100 | 5 | 2 | 20 | 1 | 20 | 20 | 0 |
| 7 | 200 | 20 | 10 | 2 | 17 | 12 | 4 | 20 |
| 8 | 2000 | 0 | 10 | 5 | 29 | 0 | 0 | 0 |

Secondary Amines

The secondary amines useful as raw materials in the preparation of the compounds of the present invention are items of commerce available from a variety of sources, including Nova Molecular Technologies, Janesville, Wis. They conform to the following structure:

wherein:
R$^1$ and R$^2$ are CH$_3$—(CH$_2$)$_e$;
e and integer ranging from 0 to 21.

EXAMPLES OF AMINES

| Examples | e |
|---|---|
| 9 | 0 |
| 10 | 1 |
| 11 | 2 |
| 12 | 3 |
| 13 | 17 |
| 14 | 21 |

General Process

To a suitable reaction flask equipped with stirring, heat and a reflux condenser, is added the required amount of the specifie[0084] silicone epoxide (examples 1–8). Isopropanol, totaling 10% by weight of the total quantity of material being produced is then added. The specified amount and type of amine (examples 9–14) is then added under agitation. The resulting reaction mass is heated to 80–100° C. The reaction mass is held at this temperature for six hours, during which time the epoxide value drops to vanishingly low levels and the tertiary amine concentration reaches theoretical. The isopropanol is then striped off using vacuum.

Example

| | Silicone Epoxide | | Secondary Amine | |
|---|---|---|---|---|
| Example | Example | Grams | Example | Grams |
| 15 | 1 | 9426.0 | 9 | 574.0 |
| 16 | 2 | 8697.0 | 10 | 1303.0 |
| 17 | 3 | 782.4 | 11 | 217.6 |
| 18 | 4 | 722.9 | 12 | 277.1 |
| 19 | 5 | 373.5 | 13 | 626.5 |
| 20 | 6 | 941.8 | 14 | 58.2 |
| 21 | 7 | 986.3 | 10 | 13.7 |
| 22 | 8 | 992.9 | 10 | 7.1 |

Oxidation of Tertiary Amines to Amine Oxides

Next, in a subsequent process, the tertiary amine prepared above is oxidized to the amine oxide using hydrogen peroxide. The preferred hydrogen peroxide concentration is 50% by weight, but other conentrations can be used.

Hydrogen peroxide is an item of commerce, provided by many suppliers. The most important of which is DuPonte.

General Procedure

To a suitable reaction flask with heating, dropping funnel, and thermometer, is added the specified amount of the specified silicone amine (examples 15–22). Next the specified amount of water and hexylene glycol is added. Hexylene glycol is used to improve the dispersibility of the more hydrophobic materials. The reaction mass is heated to 80° C. Next the specified amount of 50% hydrogen peroxide is added slowly over a period of one to three hours. The rate of addition is slowed to accommodate foam generation. The reaction mass is held for four hours after the addition is complete. The reaction is monitored by the decrease peroxide content. The percent of unreacted hydrogen peroxide is generally below 0.1%. The product is used as prepared.

Examples 23–30

| | Silicone Amine | | 50% Hydrogen Peroxide | Water | Hexylene Glycol |
|---|---|---|---|---|---|
| Example | Example | Grams | Grams | Grams | Grams |
| 23 | 15 | 479.2 | 41.6 | 279.2 | 200.0 |
| 24 | 16 | 471.4 | 57.2 | 200.0 | 271.4 |
| 25 | 17 | 465.9 | 68.3 | 232.9 | 232.9 |
| 26 | 18 | 466.0 | 68.1 | 365.9 | 100.0 |
| 27 | 19 | 480.3 | 39.3 | 240.2 | 240.2 |
| 28 | 20 | 498.5 | 3.1 | 199.4 | 299.0 |
| 29 | 21 | 497.0 | 6.1 | 248.5 | 248.5 |
| 30 | 22 | 498.9 | 2.2 | 149.5 | 349.4 |

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A silicone amine oxide conforming to the following structure:

$$CH_3-Si(CH_3)_2-(O-Si(CH_3)_2)_a-O-(CH_2CH_2O)_x-(CH_2CH(CH_3)O)_y-(CH_2CH_2O)_z-H$$

[structure with $(CH_2)_3$, $(O-Si(CH_3))_b$, $(O-Si((CH_2)_3)-)_c$, $(O-Si((CH_2)_n)-)_d$, $O-Si(CH_3)_3$ branches and terminal $CH_2-CH(OH)-CH_2-N(R^1)(R^2) \to O$]

wherein:

$R^1$ and $R^2$ are $CH_3-(CH_2)_e$;

a is an independent integer ranging from 0 to 2,000;

b and d are independent integers, each ranging from 0 to 20;

c is an integer ranging from 1 to 20, x, y and z are independent integers, each ranging from 0 to 20;

n is an integer ranging from 1 to 29 e is an integer ranging from 0 to 21.

2. A silicone amine oxide of claim 1 wherein b is 0.

3. A silicone amine oxide of claim 1 wherein b is 1 to 20.

4. A silicone amine oxide of claim 1 wherein d is 0.

5. A silicone amine oxide of claim 1 wherein d is 1 to 20.

6. A silicone amine oxide of claim 1 wherein both b and d are 0.

7. A silicone amine oxide of claim 1 wherein e is 17.

8. A silicone amine oxide of claim 1 wherein e is 1.

9. A silicone amine oxide of claim 1 wherein e is 0.

10. A silicon[0085] amine oxide of claim 1 wherein e is 11.

11. A silicone amine oxide of claim 1 wherein e is 17.

12. A silicone amine oxide of claim 1 wherein e is 21.

13. A silicone amine conforming to the following structure;

$$CH_3-Si(CH_3)_2-(O-Si(CH_3)_2)_a-O-(CH_2CH_2O)_x-(CH_2CH(CH_3)O)_y-(CH_2CH_2O)_z-H$$

[structure with $(CH_2)_3$, $(O-Si(CH_3))_b$, $(O-Si((CH_2)_3)-)_c$, $(O-Si((CH_2)_n)-)_d$, $O-Si(CH_3)_3$ branches and terminal $CH_2-CH(OH)-CH_2-N(R^1)(R^2)$]

wherein:

$R^1$ and $R^2$ are $CH_3-(CH_2)_e$;

a is an independent integer ranging from 0 to 2,000;

b and d are independent integers, each ranging from 0 to 20;

c is an integer ranging from 1 to 20;

x, y and z are independent integers, each ranging from 0 to 20;

n is an integer ranging from 1 to 29.

14. A silicone amine oxide of claim 13 wherein b is 0.

15. A silicone amine oxide of claim 13 wherein b is 1 to 20.

16. A silicone amine oxide of claim 13 wherein d is 0.

17. A silicone amine oxide of claim 13 wherein d is 1 to 20.

18. A silicone amine oxide of claim 13 wherein both b and d are 0.

* * * * *